United States Patent [19]

Beck

[11] Patent Number: 4,632,973

[45] Date of Patent: Dec. 30, 1986

[54] METHOD OF IMPROVING FLAME RESISTANCE OF EPOXY RESINS AND RESULTING COMPOSITIONS

[75] Inventor: H. Nelson Beck, Walnut Creek, Calif.

[73] Assignee: The Dow Chemical Company, Midland, Mich.

[21] Appl. No.: 789,898

[22] Filed: Oct. 18, 1985

[51] Int. Cl.$^4$ .............................................. C08G 59/20
[52] U.S. Cl. ....................... 528/98; 528/103; 528/398
[58] Field of Search ................ 528/103, 398, 98

[56] References Cited

U.S. PATENT DOCUMENTS

| | | | |
|---|---|---|---|
| 2,627,521 | 2/1953 | Coover | 260/348 |
| 2,856,369 | 10/1958 | Smith et al. | 528/398 |
| 2,965,607 | 12/1960 | Martin et al. | 260/47 |
| 3,035,021 | 5/1962 | Howe | 260/47 |
| 3,520,832 | 7/1970 | Vogt et al. | 528/103 |
| 3,558,668 | 1/1971 | Hochreuter et al. | 528/398 X |
| 3,661,857 | 5/1972 | Kerst | 528/398 X |
| 3,859,255 | 1/1975 | Heer et al. | 260/51 EP |
| 4,164,487 | 8/1979 | Martin | 260/29.2 EP |
| 4,256,844 | 3/1981 | Martin et al. | 521/59 |
| 4,394,496 | 7/1983 | Schrader | 528/98 |

OTHER PUBLICATIONS

Kirk–Othmer, vol. 9, pp. 267–289 (1980).

*Primary Examiner*—Earl Nielsen
*Attorney, Agent, or Firm*—Robert R. Stringham

[57] ABSTRACT

Epoxy resins reacted with an oxirane group containing phosphonate of the formula:

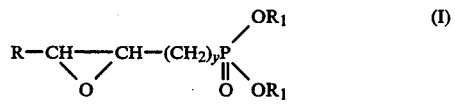

wherein R is hydrogen or lower alkyl and $R_1$ is lower alkyl are described. The backbone of the epoxy resin contains a functional substituent which reacts with (I) preferably a hydroxyl substituent. The cured epoxy resins reacted with the phosphonate (I) have improved flame resistance or glass temperatures.

24 Claims, 2 Drawing Figures

METHOD OF IMPROVING FLAME RESISTANCE OF EPOXY RESINS AND RESULTING COMPOSITIONS

BACKGROUND OF THE INVENTION

(1) Field of the Invention

The present invention relates to novel epoxy resins which are flame resistant prepared from an oxirane containing phosphonate of the formula:

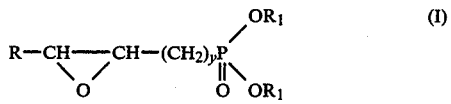

wherein R is hydrogen or lower alkyl, $R_1$ is lower alkyl and y is 1 to 3, and wherein in the oxirane group of the phosphonate reacts with a functional substituent in the backbone of the epoxy resin. In particular the present invention relates to epoxy resins prepared from dimethyl (oxiranylmethyl) phosphonate wherein the backbone of the epoxy resin contains a hydroxyl group, preferably substituted in an alkylene group as the functional substituent.

(2) Prior Art

U.S. Pat. No. 2,627,521 to Coover (1953) describes the use of oxirane containing phosphonates in cellulose derivatives and polyvinyl resins as plasticizers and stabilizers. The phosphonates are also indicated to be polymerizable. The literature describes numerous uses of phosphorus containing organic compounds with polyurethane and epoxy resins for imparting flavor resistance. It is believed that the prior art does not describe the use of phosphonates (I) which react with a functional substituent in the backbone of the epoxy resin.

Objects

It is therefore an object of the present invention to provide a method for preparing a flame resistant epoxy resin wherein the backbone of the epoxy resin contains a functional substituent which is reacted with an oxirane containing phosphonate. Further it is an object of the present invention to provide novel epoxy resins which are flame resistant and which exhibit unexpectedly high glass temperatures (Tg). Further still it is an object of the present invention to provide a method for preparing flame resistant epoxy resins which is simple and economical. These and other objects will become increasingly apparent by reference to the following description and the drawings.

In the Drawings

General Description

Figure 1:
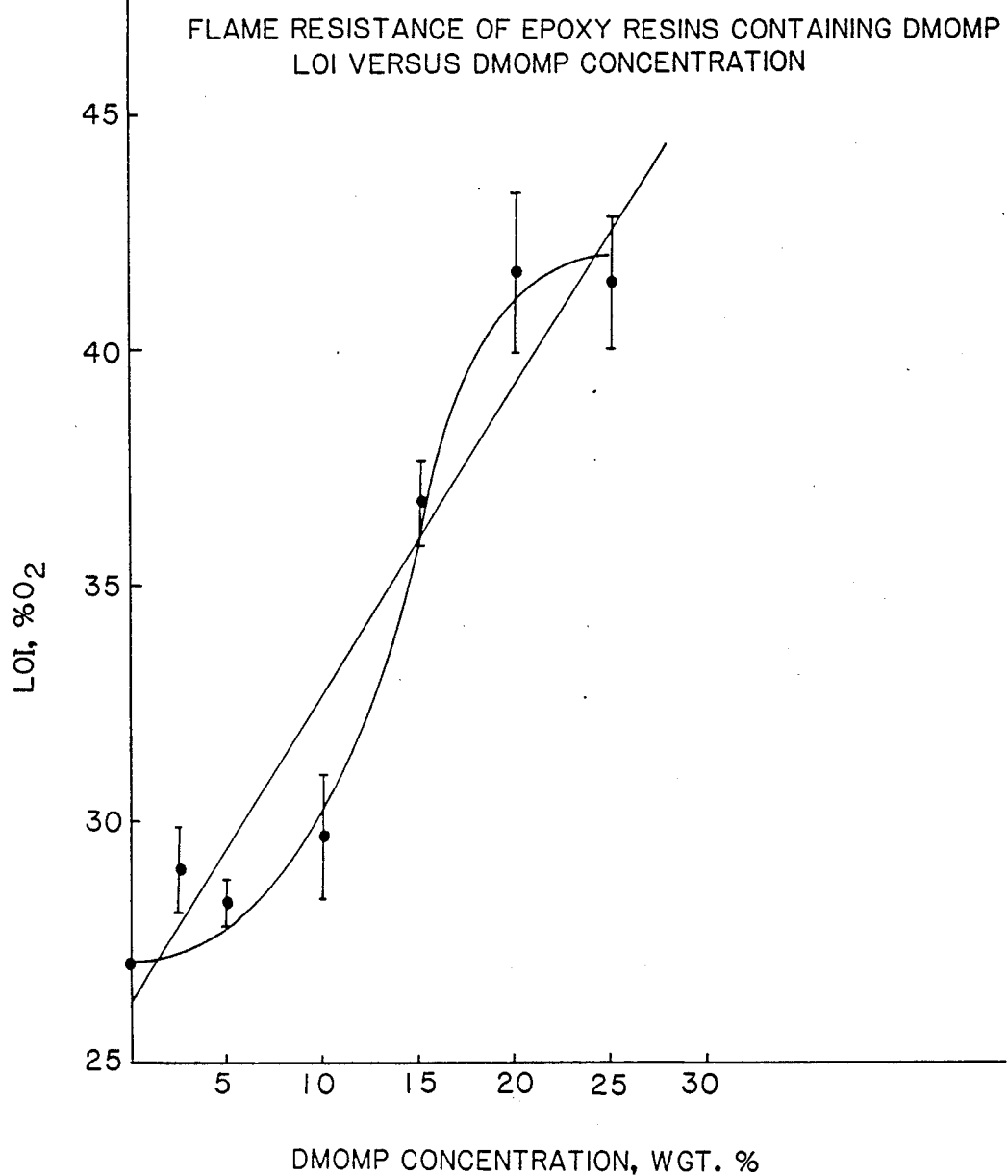
FIG. 1 is a graph showing the Limiting Oxygen Index (LOI) as a function of dimethyl (oxiranyl) methyl phosphonate (DMOMP) concentration in DER®331 which contains hydroxy alkylene groups in the backbone.

The present invention relates to an improvement in a method for imparting flame resistance to a cured epoxy resin prepared by reacting an uncured di- or polyepoxide with a curing agent wherein the di- or polyepoxide has a backbone which contains a functional substituent which is reactive with an oxirane group, the improvement which comprises: reacting an oxirane group containing phosphonate of the formula:

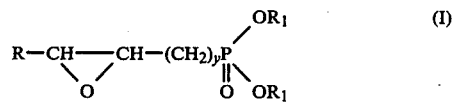

wherein the oxirane group is reactive with the functional substituent, R is hydrogen or a lower alkyl group, $R_1$ is a lower alkyl group, and y is 1, 2 or 3, in admixture with the uncured di- or polyepoxide; and reacting the admixture at elevated temperatures to produce the cured epoxy resin which is flame resistant. The preferred oxirane containing phosphonate is dimethyl (oxiranyl) methyl phosphonate.

The present invention also relates to a curable epoxy resin formulation which comprises: a liquid di- or polyepoxide composition curable with a curing agent at elevated temperatures wherein the di- or polyepoxide has a backbone which contains a functional substituent which is reactive with an oxirane group; and an oxirane group containing phosphonate of the formula:

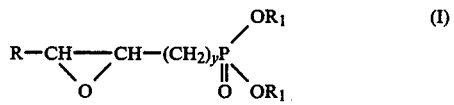

wherein the oxirane is reactable with the functional substituent, R is hydrogen or a lower alkyl group, $R_1$ is a lower alkyl group and y is 1, 2 or 3 and wherein the composition contains between about 1 and 20% by weight of the phosphonate and wherein the phosphonate imparts enhanced flame resistance to the epoxy resin formulation when cured. Finally the present invention includes the cured epoxy resins prepared with the phosphonate (I).

The oxirane containing phosphonates (I) are prepared by known processes. The general process of U.S. Pat. No. 2,627,521 of Coover can be used to prepare these compounds. In the preferred compounds, $R_1$ is a lower alkyl group containing 1 to 4 carbon atoms. R is lower alkyl containing 1 to 4 carbon atoms or hydrogen. R substituted with hydrogen is preferred. It is also preferred that $R_1$ is methyl. As previously indicated, the most preferred compound is dimethyl (oxiranylmethyl) phosphonate which is also known as dimethyl-2,3-epoxypropyl phosphonate.

Epoxy resins are generally described in Kirk-Othmer Vol 9 pages 267 to 289 (1980). The literature describing epoxy resins is extensive and only requires a general summary here. This class of resins includes di-and polyepoxides which are cured with catalytic or reactive curing agents. The backbones of the di- or polyepoxides can be aliphatic, cycloaliphatic, aromatic or heterocyclic and can include functional groups in the backbone which react with an oxirane group of the phosphonate (I) such as hydroxy, acidic ether, ester, amide and imide groups. An epoxy group in the backbone of a polyepoxide can also react with the phosphonate (I) and not interfere with the curing of the polyepoxide.

The catalytic curing agents include Lewis acids and bases which initiate homopolymerization. The boron trifluoride amine catalysts are the most common. The coreactive catalysts are polyfunctional compounds containing active hydrogens which react with the epoxy groups. Polyamines are a common class of coreactive curing agents.

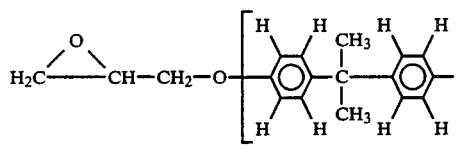

(II)

wherein n is a number between 0 and 40. This class of diepoxides includes DER ®331 (Dow Chemical Company, Midland, Michigan) which is a partial hydrolyzate of (II) where the average value of n is about 0.15. The preferred range is between about 0 and 0.15. U.S. Pat. No. 4,164,487 to Martin describes this class of epoxy resins. The backbone of these epoxy resins has a secondary hydroxyl substituent in the alkylene —$CH_2CH(OH)$— group which is reactive with the oxirane group containing phosphonate (I) of the present invention.

U.S. Pat. No. 4,364,496 to Schrader describes preferred polyglycidyl ethers of tris (hydroxyphenyl)alkanes which include a secondary hydroxyl substituent in the alkylene (—$CH_2CH(OH)$—) group of the backbone which is reactive with the oxirane group containing phosphonate (I). Preferred oligomers have the formula:

oxirane phosphonate (I). These are commercially available resins including Apogen ® Shaefer Chemicals, Inc., Riverton, New Jersey, Methylon ® Resin 75108 sold by General Electric and described in U.S. Pat. No. 2,965,607 to Martin. Other epoxy resins of this type are described in U.S. Pat. Nos. 3,035,021 to Howe, 3,859,255 to Heer and U.S. Pat. No. 4,394,496 to Schrader.

The epoxy resins can be modified to include amide (—$CONH_2$) and imide (—CO—NH—CO—) groups which are reactive with the oxirane phosphonate (I). The hydantoin epoxy resins and triazine epoxy resins include carbonyl and epoxy groups which can be hydrolyzed to hydroxy groups which are reactive with the oxirane phosphonate. Numerous variations will occur to those skilled in the art.

SPECIFIC DESCRIPTION

EXAMPLES 1 TO 11

Epoxy resins were prepared from DER ®331 (epoxy equivalent weight 189) and methylenedianiline, MDA,

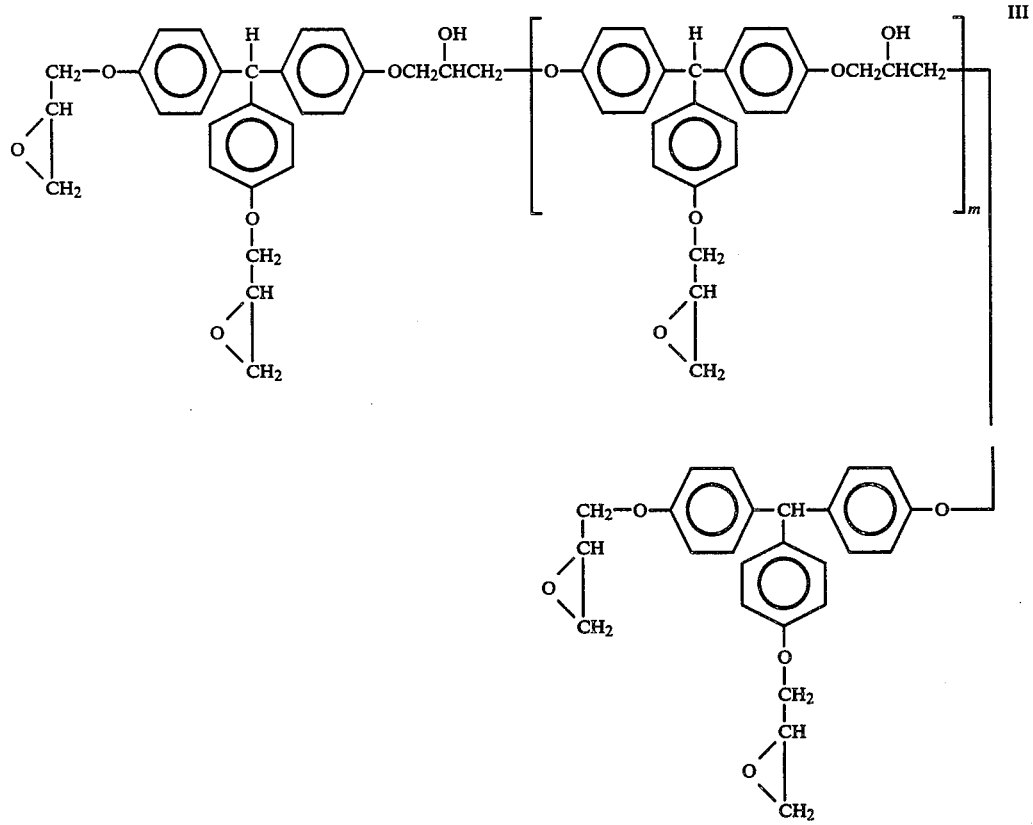

wherein m is 0, 1 or 2.

U.S. Pat. No. 4,256,844 to Martin also describes other epoxides having hydroxy, alkoxy alkyl and hydroxy alkyl groups in the aromatic rings as substituents in the backbone of the epoxy resin which are reactive with the (epoxy equivalent weight 49.57). DMOMP (epoxy equivalent weight 166.11) was prepared by an Arbuzov reaction (Merck Index, Eight Edition, page ONR60 and 61 (1976)) between trimethyl phosphite and epibromohydrin which is essentially described in U.S. Pat. No. 2,627,521 to Coover. After vacuum distillation the product refractive index was 1.4462 at 23.0° C.

The mixtures described in Table I were prepared at approximately 100° C. The ratio of methylenedianiline equivalents to total epoxy equivalents was kept constant at 0.90 for comparative purposes. The mixtures were poured into a brass mold approximately ⅛" thick and heated in an air-circulating oven at 103°–104° C. for 2.0–2.7 hours followed by heating at 182°–185° C. for 17–21 hours. Samples that contained 25–30% DMOMP were heated for longer times at lower temperatures and then slowly heated up to the final cure temperature. Limiting oxygen index (LOI) values were obtained on specimens (3 to 4×6 to 7×60 to 70 mm according to ASTM Designation D-2863-70. This method tests the burning of a sample as a function of increasing oxygen concentrations in nitrogen. Glass temperatures (Tg) were obtained at a heating rate of 20° C./min. using a Perkin-Elmer differential scanning calorimeter, Model DSC-1B.

Table I describes the composition, LOI, and Tg of epoxy resins prepared from DER ®331, DMOMP, and MDA. Resins were prepared containing up to 30 percent by weight DMOMP.

for a similar one containing 15 weight percent of the DMOMP reacted with the DER ®331.

TABLE II

| | TENSILE PROPERTIES$^f$ OF EPOXY RESINS | | | |
|---|---|---|---|---|
| Example$^a$ | DMOMP Concentration$^b$ | Tensile Strength$^{c,d}$ | Elongation$^{c,e}$ | Modulus$^d$ |
| 2 | 0 | 8510 ± 1780 | 8.5 ± 2.2 | 201700 ± 74900 |
| 7 | 15 | 3920 ± 620 | 4.6 ± 1.4 | 222300 ± 30600 |

$^a$See Table I.
$^b$Weight percent.
$^c$At break.
$^d$Pounds per square inch.
$^e$Percent.
$^f$The "±" designates the standard deviation The presence of the fire retardant results in a loss in tensile strength of about fifty percent at fifteen percent DMOMP. DMOMP also results in somewhat lower elongation and a slightly higher modulus. These observations are consistent with an increase in crosslink density and in glass temperature. The monofunctional nature of DMOMP most likely contributes to the reduced tensile strength. These properties do not interfere with the usefulness of the cured epoxy resins of the present invention in most use settings where tensile strength is

TABLE I

| | COMPOSITION AND PROPERTIES OF EPOXY RESINS CONTAINING DMOMP | | | | | | | |
|---|---|---|---|---|---|---|---|---|
| | DER ® 331 | | DMOMP | | MDA | | | |
| Example | Wgt. | Conc. | Wgt. | Conc. | Wgt. | Conc. | LOI$^a$ | Tg$^b$ |
| 1 | 41.1 g | 80.92% | — | — | 9.694 g | 19.08% | 27.0 ± 0.0 | 139.0 ± 1.0° C. |
| 2 | 66.002 | 80.90 | — | — | 15.580 | 19.10 | | |
| 3 | 47.353 | 78.32 | 1.524 g | 2.52% | 11.587 | 19.16 | 29.0 ± 0.9 | 171.8 ± 3.7 |
| 4 | 46.128 | 75.77 | 3.047 | 5.01 | 11.707 | 19.23 | 28.3 ± 0.5 | 185.6 ± 1.1 |
| 5 | 43.632 | 70.64 | 6.180 | 10.01 | 11.958 | 19.36 | 29.7 ± 1.3 | 179.0 ± 1.3 |
| 6 | 40.470 | 65.49 | 9.283 | 15.02 | 12.046 | 19.49 | 36.8 ± 0.9 | 177.9 ± 1.8 |
| 7 | 60.705 | 65.48 | 13.935 | 15.03 | 18.073 | 19.49 | | |
| 8 | 37.234 | 60.35 | 12.354 | 20.02 | 12.107 | 19.62 | 41.7 ± 1.7 | 152.4 ± 2.2 |
| 9 | 20.005 | 55.25 | 9.052 | 25.00 | 7.154 | 19.76 | 41.5 ± 1.4 | 106.3 ± 8.2 |
| 10 | 20.010 | 50.12 | 11.972 | 29.99 | 7.939 | 19.89 | | |
| 11 | 20.009 | 50.09 | 11.996 | 30.03 | 7.938 | 19.87 | | |

$^a$Limiting oxygen index, % oxygen.
$^b$Glass temperature determined at a scanning rate of 20° C./min.
$^c$See Table II for tensile properties.
$^d$See FIG. 3.
$^e$Heated slowly from 95 to 183¼° C. for 3¼ hours; then heated at 183¼° C. for 19¼ hours.
$^f$Heated slowly from 74 to 183° C. for 6 hours; then heated at 187° C. for 15¼ hours.
$^g$Heated slowly from 94 to 185° C. for 3¾ hours; then heated at 185° C. for 16¼ hours.

Figure 2:
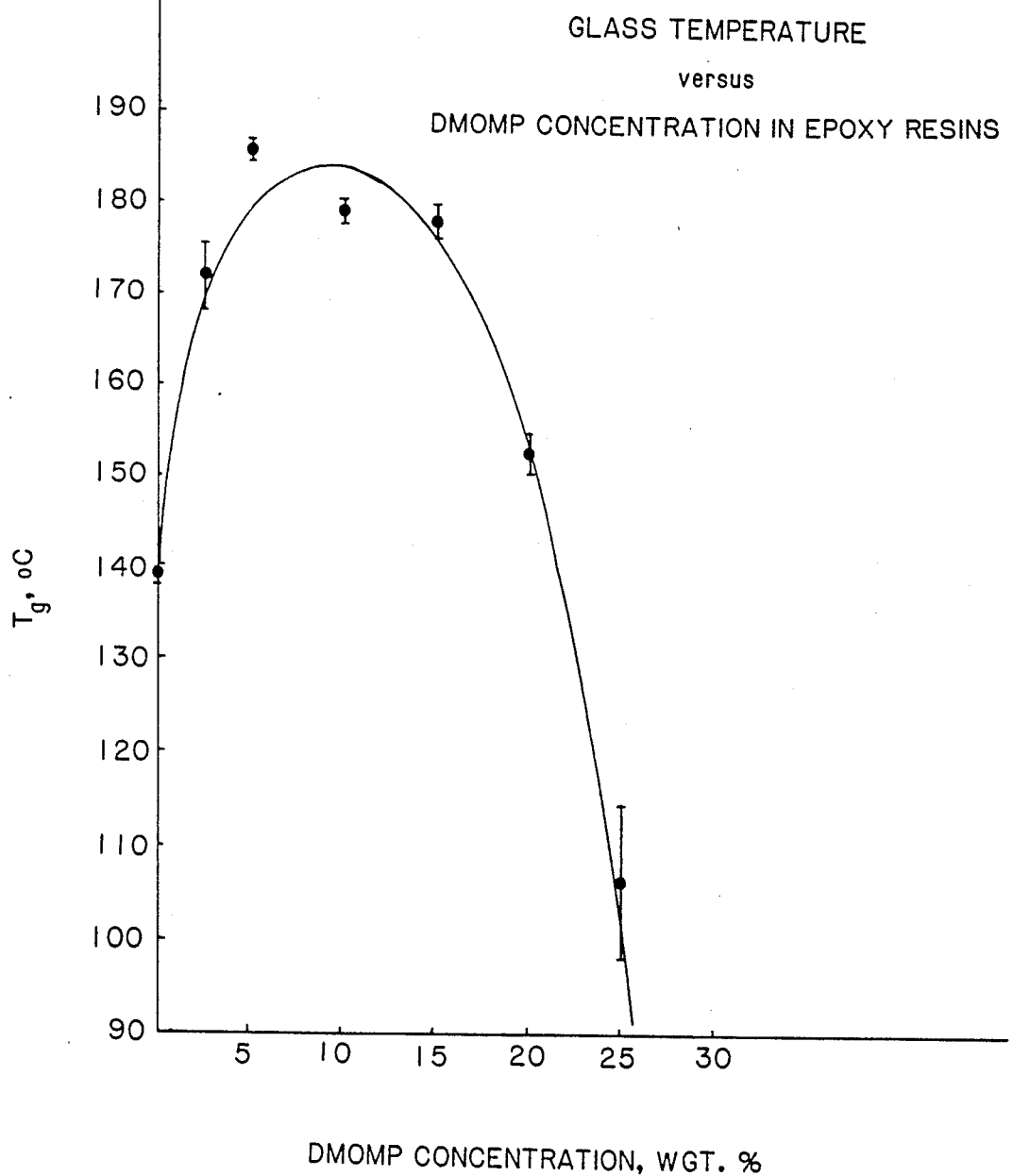
FIG. 2 is a graph showing glass temperature (Tg) as a function of the concentration of DMOMP in DER®331.

FIG. 1 which plots the results of Table 1 shows the increase in LOI of the epoxy resin with increasing concentration of DMOMP. The straight line is a least squares fit for the seven points: LOI (% $O_2$)=0.657 (DMOMP, wgt. %)+26.15; (r=0.96). FIG. 2 shows the change in glass temperature (Tg) with DMOMP concentration. Copolymerization of small amounts of DMOMP into the resin resulted in an increase in Tg from 139° C. to a maximum of about 186° C. When the concentration of DMOMP was increased above about 15 wgt. % the Tg dropped sharply until it was about 106° C. at 25% DMOMP. The peak in Tg occurred at about 5 to 15% DMOMP content. The reason for the increase and the peak in Tg with increasing DMOMP concentration is not known. The DMOMP may be reacting and copolymerizing not only through the oxiranyl group but also through the two $POCH_3$ groups, possibly with the elimination of methanol; a "tighter" and more highly crosslinked network might thus be obtained with accompanying increase in the glass temperature.

Table II lists some common tensile properties for an epoxy resin prepared from DER ®331 and MDA and not relied upon.

The heating of compostions containing DMOMP needed to be carried out with caution, since DMOMP undergoes vigorous reaction and decomposition at temperatures in excess of about 150° C. to give a black, water and toluene soluble char. At 100° C., mixtures of DER ®331 and MDA that contained greater than about 20% DMOMP produced a vigorous and exothermic decomposition/polymerization to give a black, swollen, foamed, and charred solid; the reaction was especially vigorous and more apt to occur in thicker sections or in other geometries where heat conduction was poor. Resins that contained 25 to 30% DMOMP (Examples 9, 10 and 11, Table I) were prepared by starting the polymerization reaction at temperatures below 100° C. followed by a slow and regulated temperature increase to the final curing temperature of 183° to 185° C. Compositions containing greater than 25% DMOMP (Examples 10 and 11, Table I) contained large numbers of flat, opaque, and dark discs measuring about 3 to 5 mm diameter. These resins were brittle and had dimpled surfaces where the discs touched the surface. The composition of the discs is not known. A violent reaction was observed between DMOMP, 10 g, and MDA, 2.7 g, in an aluminum weighing dish within five minutes at 105° to 110° C. The color of the clear, cured resins became progressively darker with increasing DMOMP concentration.

Epoxy resins containing no DMOMP burned in 27% oxygen giving a fluffy soot with a negligible amount of char formation. The presence of DMOMP resulted in a stiff free-standing and voluminous char. The presence of 20 to 25% DMOMP resulted in a resin that ignited and burned with difficulty; the composition burned erratically with sputtering.

As can be seen from the preceding Examples, Dimethyl(oxiranylmethyl)phosphonate, DMOMP, was found to be an effective fire retardant when copolymerized with DER ®331 and a curing agent such as methylenedianiline to produce a cured epoxy resin. A maximum in beneficial effect was observed at a concentration of about 15 weight percent DMOMP; the LOI increased from 27 to 37% oxygen, and the glass temperature increased from 139° to 178° C. Tensile strength, at 15 percent DMOMP, suffers, but elongation and modulus were not affected significantly. At concentrations of DMOMP in excess of about 20 percent the benefits from increased fire resistance were offset by decreases in glass temperature and by difficulties in controlling the curing reaction.

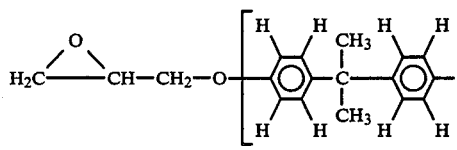

The oxirane containing phosphonates (I) are preferably provided in the epoxy resin in an amount between about 1 to 20 percent by weight of the resin, most preferably between 2 and 15 percent by weight. This provides usable cured epoxy resins.

DMOMP is a monofunctional compound that contains only one reactive group, the oxiranyl ring. Such compounds are known in polymer chemistry as "end-blocking" or chain terminating materials that control the polymer chain length or molecular weight. The higher the concentration of chain terminator the lower the molecular weight of the resulting polymer. Lower molecular weights are accompanied by poorer physical properties, e.g. tensile strength and glass temperature. Surprisingly the resins containing DMOMP have higher glass temperatures (up to about 22% DMPMP concentration). Other phosphonates (I) can produce the same results.

It is intended that the foregoing description be only illustrative of the present invention and that the invention be limited only by the hereinafter appended claims.

I claim:

1. In a method for imparting flame resistance to a cured epoxy resin prepared by reacting an uncured di- or polyepoxide with a curing agent wherein the di- or polyepoxide has a backbone which contains a functional substituent which is reactive with an oxirane group, the improvement which comprises:
   (a) reacting an oxirane group containing phosphonate of the formula:

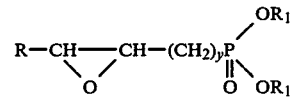

wherein the oxirane group is reactive with the functional substituent, R is hydrogen or a lower alkyl group, $R_1$ is a lower alkyl, and y is 1, 2 or 3 in admixture with the uncured di- or polyepoxide; and
   (b) reacting the admixture at elevated temperatures to produce the cured epoxy resin which is flame resistant.

2. The method of claim 1 wherein the uncured epoxy resin backbone contains a secondary hydroxyl substituent as the functional substitutent.

3. The method of claim 2 wherein the secondary hydroxyl substituent is in an alkylene group in the backbone.

4. The method of claim 1 wherein the epoxide is a diepoxide having the formula:

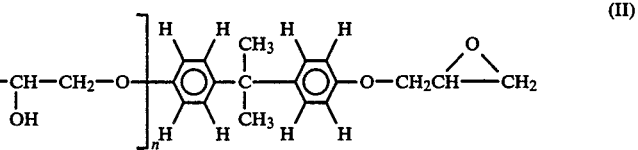

(II)

wherein n is a number between 0 and 40.

5. The method of claim 4 wherein the epoxide contains a partial hydrolyzate of the diepoxide epoxy groups and wherein the average value of n is a number between about 0 and 0.15.

6. The method of claim 5 wherein n has an average value of about 0.15.

7. The method of claim 1 wherein in the phosphonate R is hydrogen, $R_1$ is methyl and y is 1.

8. The method of claim 1 wherein the epoxide is a diepoxide having the formula:

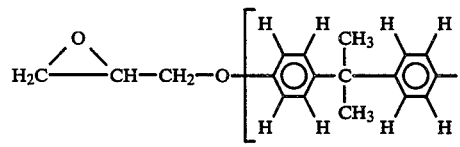

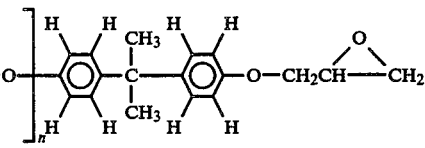

wherein n is a number between 0 and 40 and wherein in the phosphonate R is hydrogen, $R_1$ is methyl and y is 1.

9. The method of claim 8 wherein the diepoxide contains a partial hydrolyzate of the diepoxide epoxy groups and wherein the average value of n is a number between about 0 and 0.15.

10. The method of claim 9 wherein n has an average value of about 0.15.

11. The method of claim 1 wherein the phosphonate is provided in admixture with the uncured di- or polyepoxide in an amount between about 1% and 20% by weight.

12. The method of claim 1 wherein the phosphonate is provided with the di- or polyepoxide in an amount between about 2 and 15% by weight.

13. The method of claim 1 wherein the epoxide has the formula:

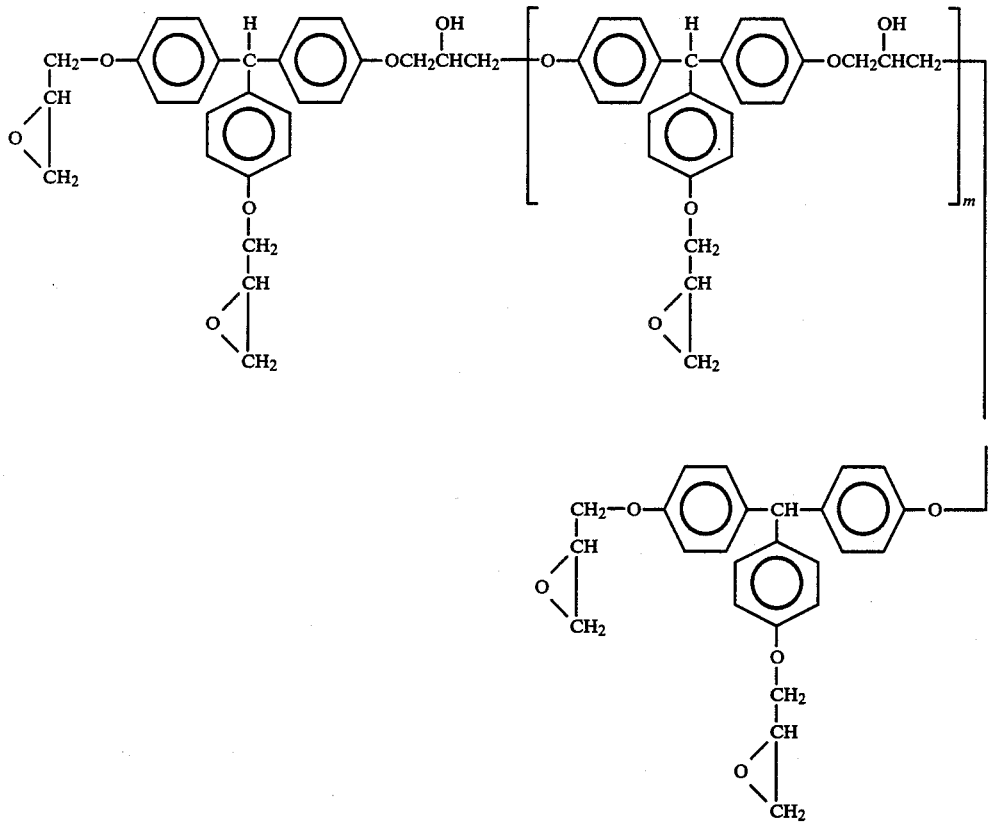

wherein m is 0, 1 or 2.

14. A curable epoxy resin formulation which comprises:

(a) a liquid di- or polyepoxide composition curable with a curing agent at elevated temperatures wherein the di- or polyepoxide has a backbone which contains a functional substituent which is reactive with an oxirane group; and (b) an oxirane group containing phosphonate of the formula:

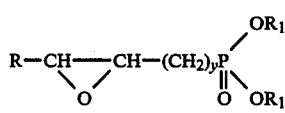

wherein the oxirane is reactable with the functional substituent, R is hydrogen or a lower alkyl group, $R_1$ is a lower alkyl group and y is 1, 2 or 3 and wherein the composition contains between about 1 and 20% by weight of the phosphonate and wherein the phosphonate imparts enhanced flame resistance to the epoxy resin formulation when cured.

15. The epoxy resin formulation of claim 14 which is cured.

16. The epoxy resin formulation of claim 14 wherein the epoxide is a diepoxide having the formula;

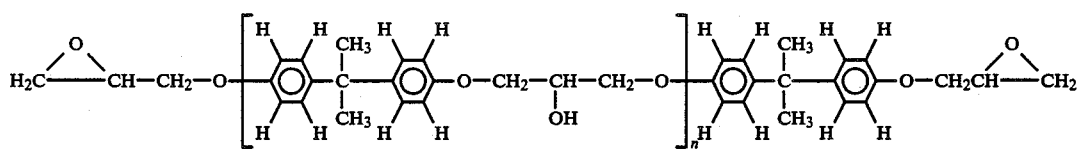

wherein n is a number between 0 and 40 and wherein in the phosphonate R is hydrogen, $R_1$ is methyl, and y is 1.

17. The resin formulation of claim 16 wherein the diepoxide contains a partial hydrolyzate of the diepoxide epoxy groups and wherein the average value of n is between about 0 and 0.15.

18. The resin formulation of claim 17 wherein n has an average value of about 0.15.

19. The resin formulation of claim 14 wherein the epoxide has the formula:

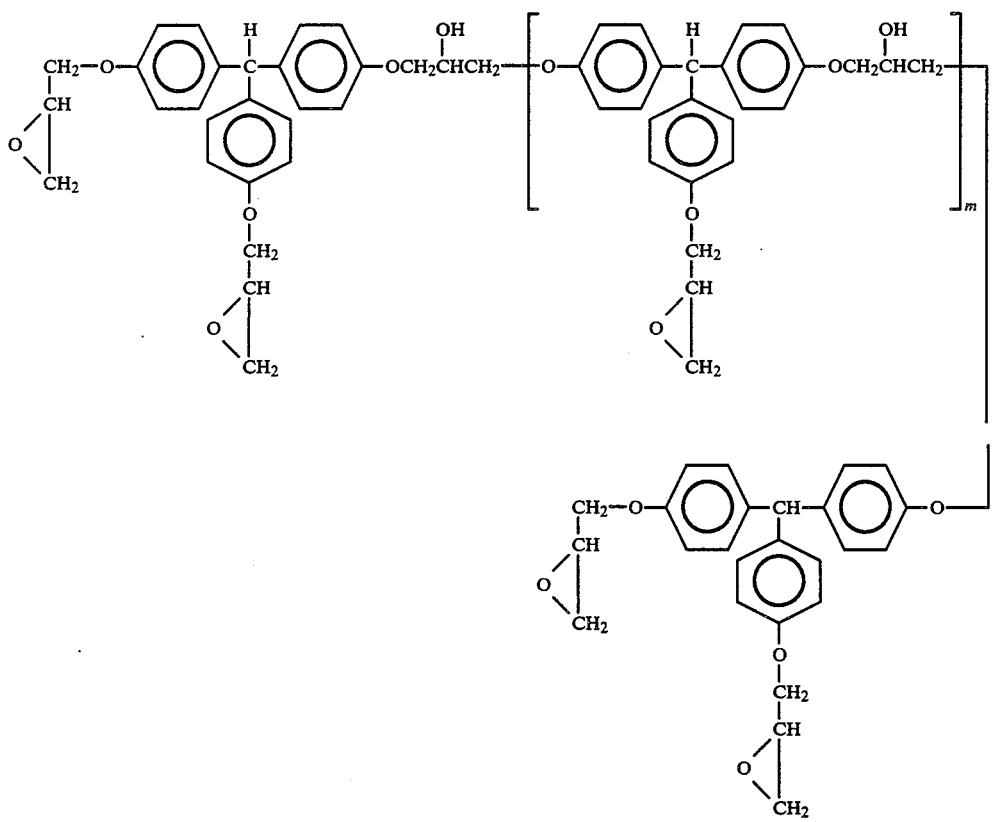

wherein m is 0, 1 or 2.

20. The resin formulation of claim 14 wherein there is an average of between about 0.1 and 1 of said functional groups per molecule of the epoxide.

21. The resin formulation of claim 14 wherein the phosphonate is present in an amount between about 2 and 15% by weight and has an increased glass temperature over the resin formulation without the phosphonate.

22. The resin formulation of claim 14 which includes an amine curing agent and is cured.

23. The resin formulation of claim 1 wherein the curable epoxy resin backbone containing a secondary hydroxyl substituent as the functinal substituent.

24. The resin formulation of claim 23 wherein the secondary hydroxyl substituent is in an alkylene portion of the backbone.

* * * * *

UNITED STATES PATENT AND TRADEMARK OFFICE
CERTIFICATE OF CORRECTION

PATENT NO. : 4,632,973

DATED : December 30, 1986

INVENTOR(S) : H. Nelson Beck

It is certified that error appears in the above-identified patent and that said Letters Patent is hereby corrected as shown below:

Column 3 at line 3, after the word "agents", the phrase -- The preferred diepoxide has the formula: -- should be added.

Column 6 at line 47, the word "compostions" should read -- compositions --.

Column 8 at line 22, the word "substitutent" should read -- substituent --.

Column 7 at line 29, after the formula, -- (II) -- should be added.

Column 12 at line 39, the word "functinal" should read -- functional --.

Signed and Sealed this
Twenty-fourth Day of November, 1987

Attest:

DONALD J. QUIGG

Attesting Officer

Commissioner of Patents and Trademarks